(12) United States Patent
Nohara et al.

(10) Patent No.: US 7,616,300 B2
(45) Date of Patent: Nov. 10, 2009

(54) EDGE FLAW DETECTION DEVICE

(75) Inventors: Naoyuki Nohara, Tokyo (JP); Hideo Sakai, Tokyo (JP)

(73) Assignee: Raytex Corporation, Tokyo (JP)

( * ) Notice: Subject to any disclaimer, the term of this patent is extended or adjusted under 35 U.S.C. 154(b) by 122 days.

(21) Appl. No.: 11/989,612

(22) PCT Filed: Aug. 10, 2005

(86) PCT No.: PCT/JP2005/014664

§ 371 (c)(1),
(2), (4) Date: Jan. 29, 2008

(87) PCT Pub. No.: WO2007/017941

PCT Pub. Date: Feb. 15, 2007

(65) Prior Publication Data
US 2009/0091748 A1    Apr. 9, 2009

(51) Int. Cl.
*G01N 21/00* (2006.01)
(52) U.S. Cl. .................. 356/237.1; 356/237.2
(58) Field of Classification Search .... 356/237.1–237.5
See application file for complete search history.

(56) References Cited

U.S. PATENT DOCUMENTS 6,476,393 B1   11/2002   Yoshida et al.
6,798,503 B2 *  9/2004   Hiramoto et al. ......... 356/237.1
2003/0184743 A1  10/2003   Hiramoto et al.

FOREIGN PATENT DOCUMENTS

| JP | 11/351850 | 12/1999 |
| JP | 2003/287412 | 10/2003 |
| JP | 2000-55815 | 2/2005 |

OTHER PUBLICATIONS

International Search Report mailed Nov. 15, 2005.

* cited by examiner

*Primary Examiner*—Michael Stafira
(74) *Attorney, Agent, or Firm*—Nixon & Vanderhye P.C.

(57) ABSTRACT

An edge flaw detection device includes an elliptical mirror having a mirror surface on the inside thereof and having a cutout that allows an object to be inserted therethrough formed at the apex thereof, a light-emitting unit that radiates coherent light toward an edge of the object arranged in the vicinity of a first focal position of the elliptical mirror, a photo detector that is arranged in a second focal position of the elliptical mirror, and a light-shielding member that shields low-order diffracted light that is reflected regularly. The light-emitting unit is moved in the thickness direction of the object by a moving member so that the light-emitting unit can radiate the coherent light in a different radiation range in the thickness direction at the edge of the object.

4 Claims, 6 Drawing Sheets

EDGE FLAW DETECTION DEVICE

This application is the U.S. national phase of International Application No. PCT/JP2005/014664, filed 10 Aug. 2005.

TECHNICAL FIELD

The present invention relates to an edge flaw detection device that optically detects a flaw at an edge of an object.

BACKGROUND ART

A detection device using an elliptical mirror is suggested as an edge flaw detection device that detects flaws such as narrow and long edge cracks, deficits, or polishing marks that are formed in edges, for example, the peripheral edges of silicon wafers. For example, a device is suggested in which a light-absorbing member is arranged on the mirror surface of an elliptical mirror, the light-absorbing member is made to absorb the low-order diffracted light that is regular reflection light, and only high-order diffracted light that is reflected irregularly by a flaw of an edge is detected by a photo detector provided in a second focal position (for example, refer to Patent Document 1). Further, a device is suggested in which, apart from a first photo detector provided in the second focal position, a second photo detector provided in the vicinity of an object set in a first focal position, enabling detection for vertical flaws and horizontal flaws by means of two light-receiving units (for example, refer to Patent Document 2).

However, although these edge flaw detection devices can detect the whole periphery of the edge of an object by rotating it, the specific position and size of the flaw in the thickness direction orthogonal to a circumferential direction remain unknown. Further, although it is possible to estimate the type of a flaw to some degree from the intensity of the light detected by a light-receiving unit, there was a limitation in discriminating from one parameter of luminous intensity for details.

Patent Document 1: Japanese Unexamined Patent Application, First Publication, No. 2003-287412

Patent Document 2: Japanese Unexamined Patent Application, First Publication, No. H 11-351850

DISCLOSURE OF INVENTION

The invention has been made in view of the aforementioned situations, and proposes an edge flaw detection device capable of detecting the specific position of a flaw at an edge of an object in the thickness direction, the size of the flaw, and the type of the flaw.

The invention provides an edge flaw detection device including an elliptical mirror having a mirror surface on an inside thereof, a light-emitting unit that radiates coherent light toward an edge of an object, the edge of the object being arranged in a vicinity of a first focal position of the elliptical mirror, a photo detector that is arranged in a second focal position of the elliptical mirror and is capable of detecting the diffracted light resulting when the radiated coherent light is reflected by the edge of the object and by the elliptical mirror so as to arrive at the second focal position, and a light-shielding member that shields low-order diffracted light which is regularly reflected among the diffracted light, a position of the light-emitting unit being freely set in a thickness direction of the object by a moving member so that the light-emitting unit can radiate the coherent light in a different radiation range in the thickness direction at the edge of the object.

According to the edge flaw detection device of this invention, it is possible to irradiate coherent light in a different radiation range in the thickness direction of the edge of the object by means of the moving member. Thus, by detecting the intensity of the diffracted light corresponding to an individual radiation range using the photo detector, the specific position of a flaw in the thickness direction and the size of the flaw can be detected.

Further, the invention provides an edge flaw detection device including an elliptical mirror having a mirror surface on an inside thereof, a plurality of light-emitting units that radiate coherent light toward an edge of an object, the object being arranged in a vicinity of a first focal position of the elliptical mirror, a photo detector that is arranged in a second focal position of the elliptical mirror and is capable of detecting the diffracted light resulting when the radiated coherent light is reflected by the edge of the object and by the elliptical mirror so as to arrive at the second focal position, and a light-shielding member that shields low-order diffracted light which is regularly reflected among the diffracted light, a plurality of the light-emitting units being provided in different positions in a thickness direction of the object, and each of a plurality of the light-emitting units being able to radiate the coherent light from a different direction, in a different radiation range in the thickness direction at the edge of the object.

According to the edge flaw detection device of this invention, it is possible to irradiate coherent light in a different radiation range in the thickness direction at the edge of the object by means of the plurality of the light-emitting units. Thus, by detecting the intensity of the diffracted light corresponding to an individual light-emitting unit, the specific position of a flaw in the thickness direction and the size of the flaw can be detected.

Moreover, in the edge flaw detection device of the above invention, the light-emitting unit may be constituted to include a light source that radiates the coherent light, and a condensing member that optically acts on the coherent light radiated from the light source so that the coherent light is radiated while the radiation range is reduced in the thickness direction at the edge of the object.

According to the edge flaw detection device of this invention, by reducing the radiation range of the coherent light that is radiated onto the edge of an object in the thickness direction, an intensity difference in the diffracted light detected by the photo detector depending on the position of a flaw in the thickness direction and the size of the flaw can be clarified when coherent light is irradiated by the light-emitting unit from a different position in the thickness direction.

Moreover, in the edge detection device of the above invention, the light-emitting unit may be able to radiate coherent light at various wavelengths.

According to the edge flaw detection device of this invention, by detecting the intensity of the diffracted light by coherent light at different various wavelengths by means of the photo detector, a fine flaw can be detected, or a flaw that could not be detected since coherent light having a long wavelength is largely absorbed, or a flaw that irregularly reflects only coherent light having a specific wavelength can be detected.

According to the invention, since the radiation range of the coherent light that is radiated from a light-emitting unit can be changed in the thickness direction of an object, the specific position of a flaw in the thickness direction of the object, and the size of the flaw can be specified. Moreover, by using coherent light at different various wavelengths, a fine flaw can be detected, or a flaw that could not be detected since coherent light having a long wavelength is largely absorbed, or a flaw that irregularly reflects only the coherent light having a specific wavelength can be detected. As a result, fine edge flaw detection can be realized.

BEST MODE FOR CARRYING OUT THE INVENTION

First Embodiment

Figure 1:
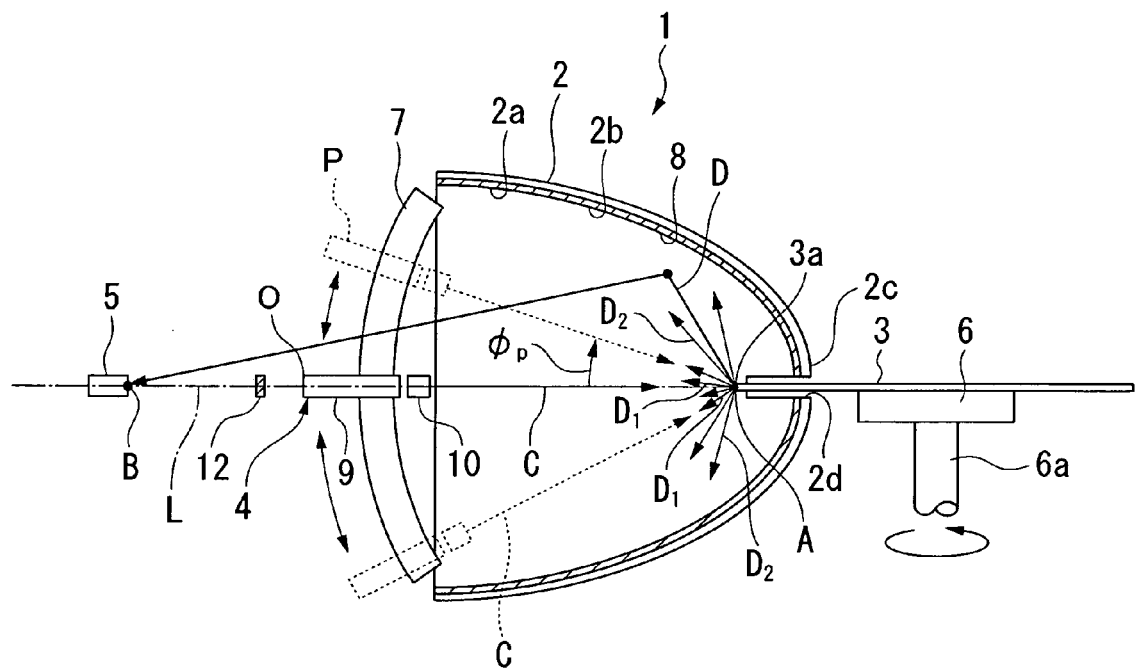
FIG. 1 is a longitudinal sectional view of an edge flaw detection device according to a first embodiment of the invention, taken along its vertical plane.
Figure 2:
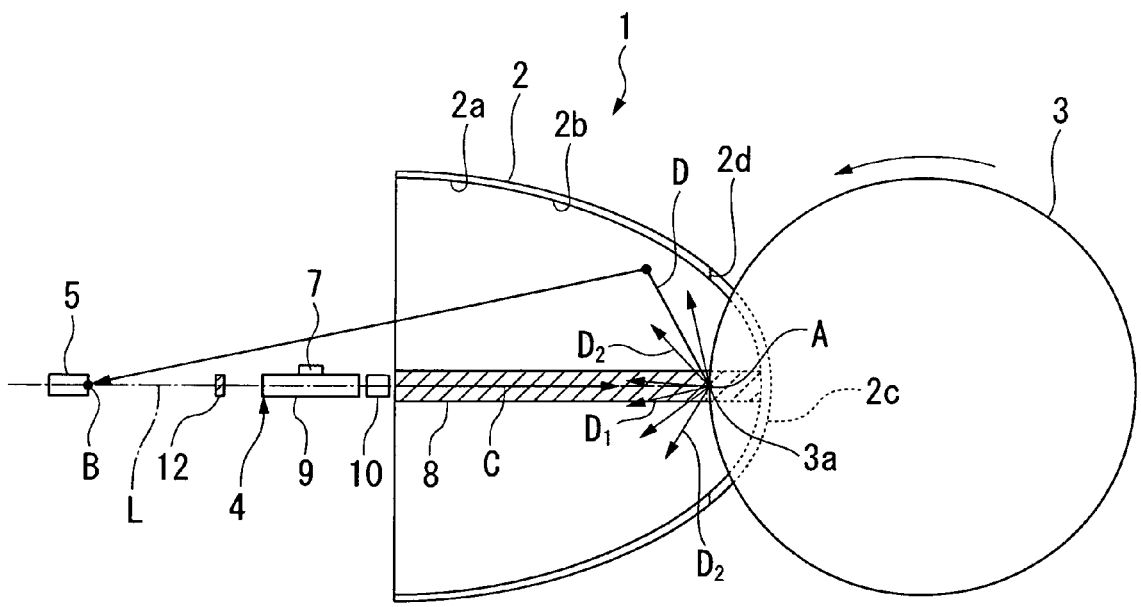
FIG. 2 is a longitudinal sectional view of the edge flaw detection device according to the first embodiment of the invention, taken along its horizontal plane.
Figure 3:
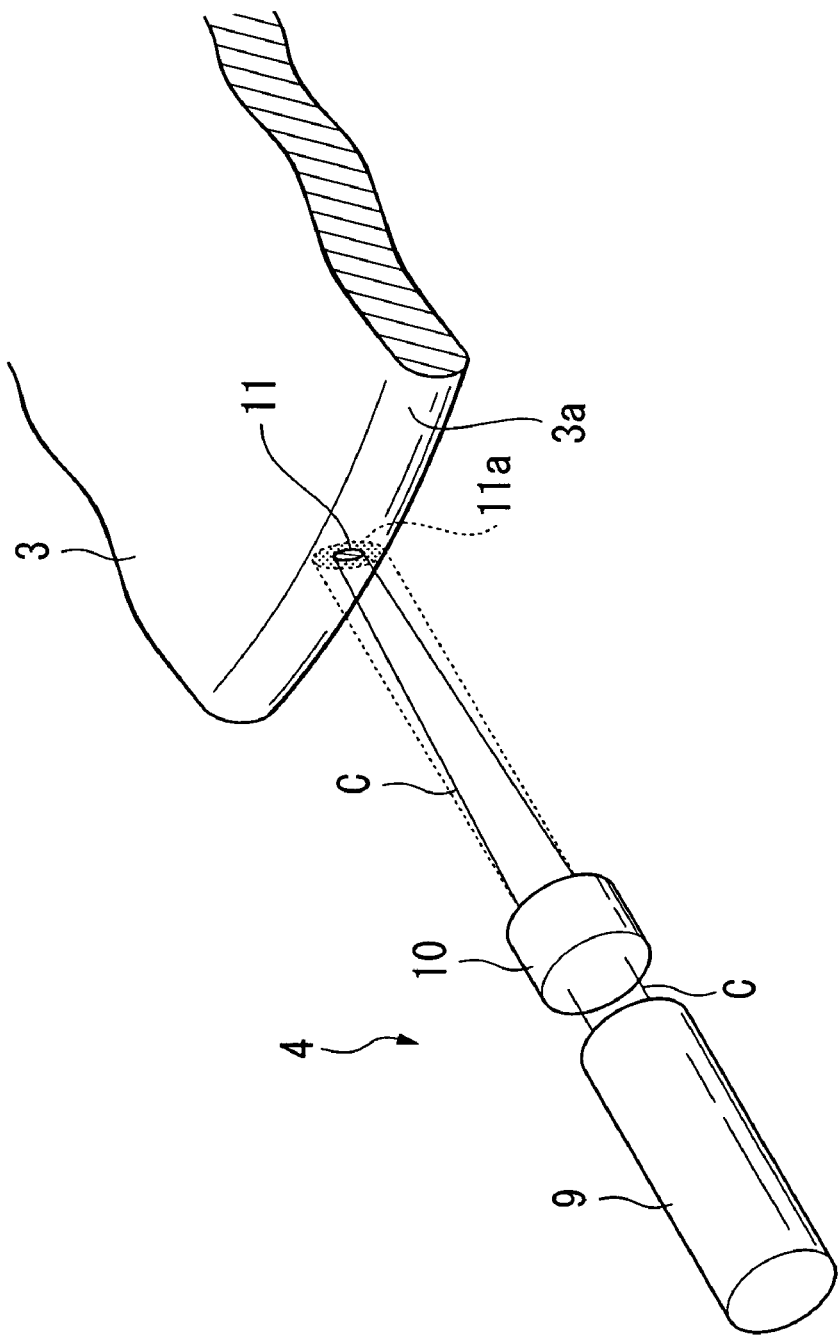
FIG. 3 is an explanatory view of the edge of an object irradiated by a light-emitting unit according to the first embodiment of the invention.
Figure 4:
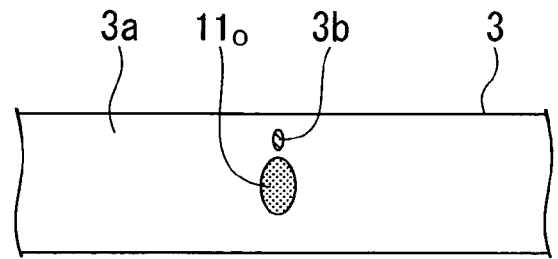
FIG. 4 is an enlarged front view of the edge of the object irradiated by the light-emitting unit according to the first embodiment of the invention.
Figure 5:
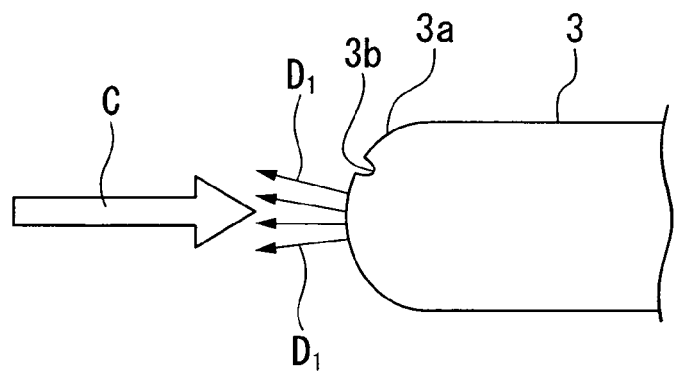
FIG. 5 is an enlarged sectional view of the edge of the object irradiated by the light-emitting unit according to the first embodiment of the invention.
Figure 6:
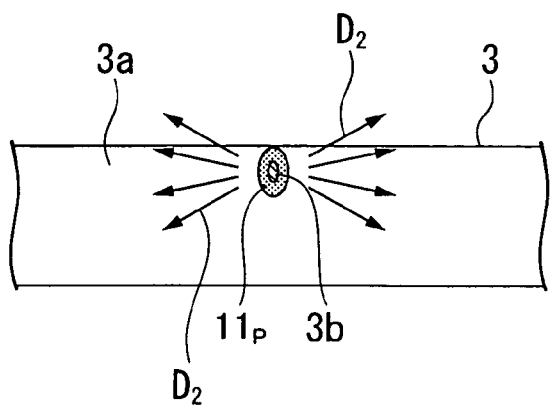
FIG. 6 is an enlarged front view of the edge of the object irradiated by the light-emitting unit according to the first embodiment of the invention.
Figure 7:
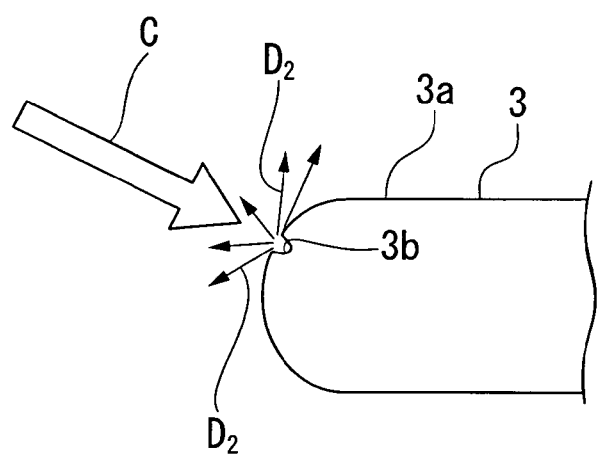
FIG. 7 is an enlarged sectional view of the edge of the object irradiated by the light-emitting unit according to the first embodiment of the invention.
Figure 8:
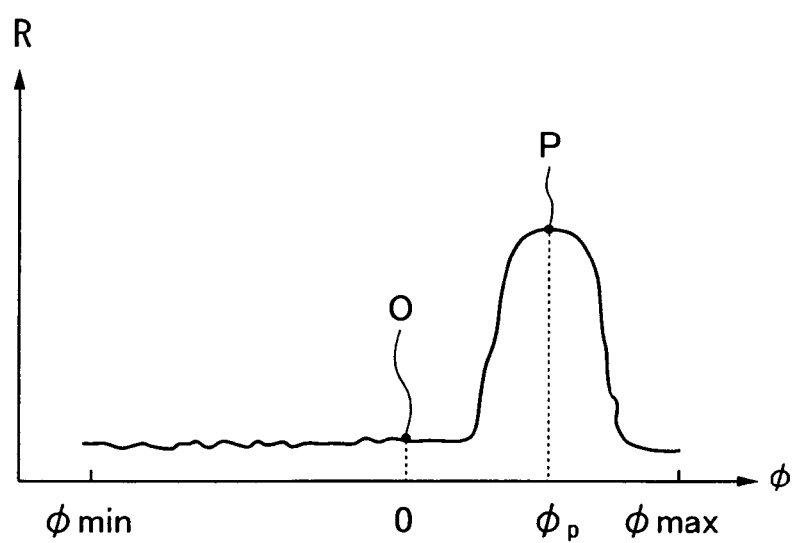
FIG. 8 is a graph illustrating an example of a detection result by a photo detector according to the first embodiment of the invention when a radiation range is changed in the thickness direction.
Figure 9:
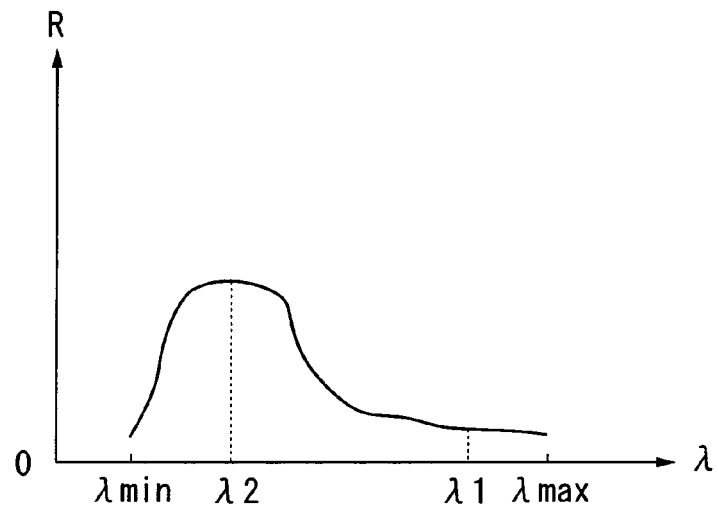
FIG. 9 is a graph illustrating an example of a detection result by the photo detector according to the first embodiment of the invention when the wavelength of the coherent light to be radiated is changed.
Figure 10:
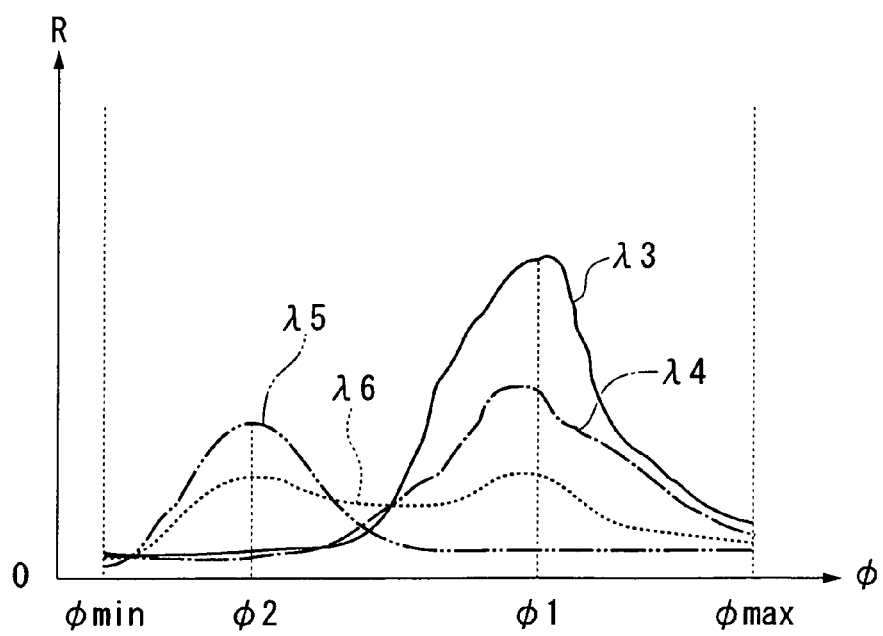
FIG. 10 is a graph illustrating an example of a detection result by a photo detector according to the first embodiment of the invention when a radiation range is changed in the thickness direction using coherent light at a plurality of wavelengths.

FIGS. 1 to 10 illustrate a first embodiment according to the invention. FIG. 1 illustrates a longitudinal sectional view of an edge flaw detection device taken along its vertical plane, and FIG. 2 illustrates a longitudinal sectional view of the edge flaw detection device taken along its horizontal plane. FIG. 3 illustrates an explanatory view of the edge of an object irradiated by a light-emitting unit. Further, FIGS. 4 and 6 illustrate the enlarged sectional views of the edge of the object, and FIGS. 5 and 7 illustrate their enlarged front views. Moreover, FIG. 8 illustrates a graph showing an example of a detection result by a photo detector when a radiation range is changed in the thickness direction, FIG. 9 illustrates a graph showing an example of a detection result by the photo detector when the wavelength of the coherent light to be irradiated is changed, and FIG. 10 illustrates a graph showing an example of a detection result by the photo detector when the radiation range is changed in the thickness direction using coherent light at a plurality of wavelengths.

As shown in FIGS. 1 and 2, the edge flaw detection device 1 includes an elliptical mirror 2 that has a mirror surface 2b at its inside 2a and has a notch 2d at an apex 2c that allows an object 3 to be inserted therethrough, a light-emitting unit 4 that irradiates coherent light C toward an edge 3a of the object 3 arranged in the vicinity of a first focal position A of the elliptical mirror 2, and a photo detector 5 that is arranged in a second focal position B of the elliptical mirror 2. Further, the edge flaw detection device 1 includes a holding portion 6 that rotatably holds the object 3, a moving member 7 that makes the light-emitting unit 4 rotatable about the first focal position A of the elliptical mirror 2 in the thickness direction of the object 3, and a light-shielding member 8 provided in the elliptical mirror 2. The object 3 is, for example, a plate-like silicon wafer, a semiconductor wafer, etc.

As shown in FIG. 3, the light-emitting unit 4 includes a light source 9 that emits coherent light C, and a condensing member 10 that optically acts on the emitted coherent light C. The light source 9 is, for example, a laser beam, and its wavelength is freely adjustable. More specifically, He—Ne lasers or semiconductor lasers are used; by enabling switching between a plurality of lasers with different wavelengths, the wavelength can be freely adjusted. Alternatively, a wavelength-variable laser may be used. Further, the condensing member 10 is a lens that reduces a radiation range 11 in the thickness direction of the edge 3a of the object 3, when the coherent light C emitted from the light source 9 is irradiated toward the edge 3a of the object 3. Above-mentioned light-emitting unit 4 can be freely set into position in the thickness direction of the object 3 by the moving member 7, and can radiate the coherent light C in different radiation ranges in the thickness direction of the edge 3a of the object 3. Further, as shown in FIGS. 1 and 2, the photo detector 5 detects the diffracted light D that is obtained when the diffracted light D, which is radiated from the light-emitting unit 4 and is reflected by the edge 3a of the object 3, is reflected by the elliptical mirror 2, and is condensed on the second focal position B, and the photo detector is a photodiode, for example.

As shown in FIGS. 1 and 2, the holding portion 6 can position the edge 3a of the object 3 in the vicinity of the first focal position A of the elliptical mirror 2, and can move the edge 3a of the object 3 in a circumferential direction on the first focal position A by rotating its rotary shaft 6a. Further, the light-shielding member 8 is a masking tape that is adhered with a predetermined width on an intersection line where a plane that is parallel to the thickness direction of the object 3 including the first focal position A and the second focal position B, and the elliptical mirror 2 intersect with each other. The diffracted light D that has reached the light-shielding member 8 will be absorbed by the light-shielding member 8, without being reflected and reaching the photo detector 5. Further, a light-shielding plate 12 is provided on the side of the first focal position A of the photo detector 5. This is provided to prevent coherent light C, radiated from the light-emitting unit 4, from being reflected by the edge 3a of the object 3 and becoming diffracted light D, but then directly reaching the photo detector 5 without being reflected by the elliptical mirror 2.

Next, the operation of the edge flaw detection device 1 will be described. As shown in FIG. 1, a case where the existence or nonexistence of any flaw is detected in an arbitrary circumferential position at the edge 3a of the object 3 is described. First, the light-emitting unit 4 is located in a central position O to irradiate the edge 3a of the object 3. FIG. 4 illustrates an enlarged front view of the edge 3a of the object 3 when being irradiated in the central position O, and FIG. 5 illustrates an enlarged sectional view. As shown in FIG. 4 and FIG. 5, when a flaw 3b is located at upper part of the edge 3a of the object 3, the flaw 3b is not included in the radiation range 11o when being irradiated from the central position O. For this reason, the radiated coherent light C is regularly reflected to be low-order diffracted light D1. The low-order diffracted light D1 heads for the second focal position B via the vicinity of the axis L in plan view as a path as shown in FIG. 2 and the light has a certain degree of spread in the thickness direction according to the shape of the edge 3a of the object 3 in side view as shown in FIGS. 1 and 5. For this reason, the low-order diffracted light D1 is absorbed by the light-shielding member 8 or the light-shielding plate 12, and much of the light does not reach the photo detector 5.

In addition, if located in the central position O to irradiate the edge 3a of the object 3 with the coherent light C as described above, the coherent light C will be radiated through the axis L of the elliptical mirror 2. Instead of this, the optical axis of the light source 9 may be arranged so as to deviate slightly (about 4 degrees) with respect to the axis L of the elliptical mirror 2 so that the light source 9 and the second focal point B may not overlap with each other. Thereby, the low-order diffracted light D1 resulting when radiated coherent light C is regularly reflected by the edge 3a of the object 3, also deviates from the axis L of the elliptical mirror 2. Thus, it is possible to omit the light-shielding plate 12.

In this case, although the optical axis of the light source 9 may be tilted in the horizontal direction with respect to the axis L of the elliptical mirror 2, it is preferably tilted in the vertical direction. This is because, when the coherent light C is radiated onto the edge face 3a of the horizontally supported object 3, from the direction tilted in the horizontal direction with respect to the axis L of the elliptical mirror 2, there is a disadvantage in that the scattered and reflected light in the lateral direction, including many kinds of information required for flaw detection, may be biased to the lateral direction, and effective information may be damaged. On the other hand, when the optical axis of the light source is tilted in the vertical direction, the scattered and reflected light in the vertical direction seldom includes information required for flaw detection. Thus, the above-described problem does not tend to occur. In addition, even when tilted in the horizontal direction, the scattered and reflected light in the lateral direction may be condensed on a photo detector by the contrivance of forming the elliptical mirror 2 into a laterally asymmetrical shape, or the like.

Next, as shown in FIG. 1, suppose that sequential irradiation is performed while the light-emitting unit 4 is moved upward and reaches an upper position P. FIG. 6 illustrates an enlarged front view of the edge 3a of the object 3 when being irradiated in the upper position O, and FIG. 7 illustrates an enlarged sectional view. As shown in FIG. 6 and FIG. 7, since the radiation range 11p overlaps a flaw 3b, the coherent light C is irregularly reflected by the flaw 3b, and becomes high-order diffracted light D2. For this reason, as shown in FIGS. 1, 2, and 7, the diffracted light D2 is not absorbed by the light-shielding member 8, but much of the light is reflected to the elliptical mirror 2, and is detected by the photo detector 5 in the second focal position B. FIG. 8 shows the relationship between the irradiation angle φ and the intensity R of the light detected by the photo detector 5 when the irradiation angle φ in the central position O is defined as zero degrees. As shown in FIG. 8, if located in the central position O or lower than the central position where the irradiation angle φ is a negative value, the low-order diffracted light D1 of regular reflection is obtained, and most of the light does not reach the photo detector 5. Thus, the intensity R of the light remains at a lower level. Moving upward from the central position O and the irradiation angle φ indicating a positive value, the flaw 3b is included in the radiation range 11. Thus, the high-order diffracted light D2 is generated as a result of the irregular reflection and the intensity R of the light increases gradually, and reaches a maximum value in the upper position P. As described above, by irradiating while the radiation range in the thickness direction of the object 3 is changed in an arbitrary edge 3a of the object 3, the information showing the position of a flaw in the thickness direction or the state (size, shape, etc.) of the flaw can be obtained. Also, if the rotary shaft 6a of the holding portion 6 is rotated and the edge 3a is moved in the circumferential direction, the existence or nonexistence of any flaw at the edge 3a of the object 3, and the position and size of the flaw can be investigated in detail in the circumferential direction and the thickness direction.

In addition, as shown in FIG. 3, if the radiation range 11a to be irradiated is set in the whole thickness direction by the switching of a lens that is the condensing member 10, detection of any flaw at an edge in the circumferential direction can be performed efficiently. That is, if detection in the thickness direction is performed while the radiation range 11 is reduced in only the portion where the existence or nonexistence of any flaw has been confirmed after the existence or nonexistence of any flaw is confirmed in the circumferential direction in the radiation range 11a, detailed detection can be performed efficiently. Here, as the condensing member 10 that changes the radiation range 11, a method of switching use of a diffusing lens system, such as a meniscus lens or a Fresnel lens, or a collecting or diffusing lens system, such as a focusing glass system can be considered. Further, this function may be given to the light-emitting unit 4.

Further, the light-emitting unit 4 can radiate the coherent light C of various wavelengths λ. For this reason, a flaw that could not be recognized since absorption is large in the coherent light C of a long wavelength λ, can be recognized by shortening the wavelength λ. FIG. 9 shows the relationship between a wavelength λ when irradiation is performed while the wavelength λ is changed, and the intensity R of the light detected by the photo detector 5, in an arbitrary position at the edge 3a of the object 3. As shown in FIG. 9, a flaw that could not be detected at a certain wavelength λ1 can be detected at a wavelength λ2, by changing the wavelength λ. FIG. 10 shows a graph in the case where the irradiation angle φ of the light-emitting unit 4 is changed and the wavelength λ is changed. Here, individual graphs represent the relationships at the time of wavelengths λ3, λ4, λ5, and λ6, and the wavelengths λ have the magnitude relationship λ3<λ4<λ5<λ6. As shown in FIG. 10, in this example, in the vicinity of an irradiation angle φ1, the high-order diffracted light D2 resulting from a flaw can be prominently detected at a small wavelength λ, and in the vicinity of an irradiation angle φ2, the high-order diffracted light D2 resulting from a flaw can be strikingly detected at a large wavelength λ.

As described above, the edge flaw detection device 1 can detect the edge 3a of the object 3 in detail not only in the circumferential direction of the object but in the thickness direction thereof, and can operate detection with changing the wavelength λ of the coherent light C that is irradiated according to the characteristics of a flaw. For this reason, the position, the size, range, and type of a flaw can be detected.

Second Embodiment

Figure 11:
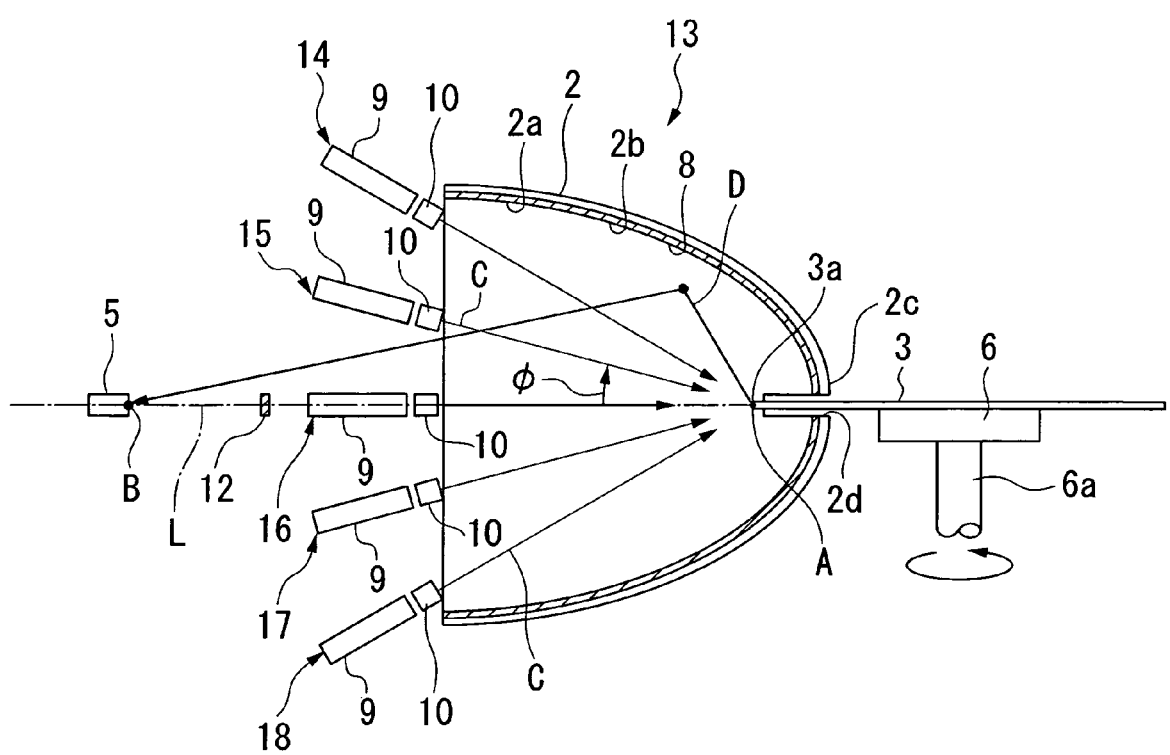
FIG. 11 is a longitudinal sectional view of an edge flaw detection device according to a second embodiment of the invention, taken along its vertical plane.

FIG. 11 shows a second embodiment of the invention and a longitudinal sectional view of an edge flaw detection device taken along its vertical plane. In this embodiment, members common to the members used in the aforementioned embodiment are denoted by the same reference numerals, and the description thereof is omitted.

The edge flaw detection device 13 in this embodiment includes a plurality of light-emitting units 14, 15, 16, 17, and 18. The light-emitting units 14, 15, 16, 17, and 18 are arrayed at substantially equal angles in the thickness direction of the object 3, and each of them has a light source 9 and a condensing member 10, and is able to irradiate the edge 3a of the object 3 in the first focal position A.

As such, even if a light-emitting unit is not movable in the thickness direction of the object 3 by a moving member, the edge 3a of the object 3 can be similarly detected in detail in the thickness direction by arranging a plurality of the light-emitting units.

Although the embodiments of the invention have been described hitherto in detail with reference to the drawing, concrete configurations are not limited to the embodiments, and the invention also includes design changes that do not depart from the spirit of the invention.

In addition, although the example where the radiation range 11 is reduced in the thickness direction of the edge 3a of the object 3 by the condensing member 10 of the light-emitting unit has been shown, the invention is not limited thereto. Since the intensity R of the light is relatively changed by changing the radiation range in the thickness direction even if the radiation range 11 is large, it is possible to identify a flaw. Further, by radiating coherent light from a different angle in the same radiation range, a difference is caused in the intensity of reflected light according to the state of a flaw that is in the radiation range. By utilizing this, it is also possible to indirectly detect the state (size, an angle, etc.) of a flaw. Further, although a masking tape adhered to the elliptical mirror 2 is adopted as the light-shielding member 8, the invention is not limited thereto. Any members may be adopted so long as they can shield the low-order diffracted light D1 that is reflected regularly. For example, a light-shielding plate consisting of a plate having a predetermined width serving as a spatial filter may be arranged between the edge 3a of the object 3 and the light source 9 so as to abut on the inner face of the elliptical mirror 2 in a vertical direction orthogonal to the face of the object 3. Although this allows the low-order diffracted light D1 to be shielded by the light-shielding plate, the high-order diffracted light D2 leaks out of the light-shielding plate, and is condensed by the elliptical mirror 2.

INDUSTRIAL APPLICABILITY

Since the radiation range of the coherent light that is radiated from a light-emitting unit can be changed in the thickness direction of an object, the specific position of a flaw in the thickness direction of the object, and the size of the flaw can be specified.

The invention claimed is:

1. An edge flaw detection device comprising:
an elliptical mirror having a mirror surface on an inside thereof;
a light-emitting unit that radiates coherent light toward an edge of an object, the edge of the object being arranged in a vicinity of a first focal position of the elliptical mirror;
a photo detector that is arranged in a second focal position of the elliptical mirror and is capable of detecting the diffracted light resulting when the radiated coherent light is reflected by the edge of the object and by the elliptical mirror so as to arrive at the second focal position; and
a light-shielding member that shields low-order diffracted light which is regularly reflected among the diffracted light,
a position of the light-emitting unit being freely set in a thickness direction of the object by a moving member so that the light-emitting unit can radiate the coherent light in a different radiation range in the thickness direction at the edge of the object.

2. An edge flaw detection device comprising:
an elliptical mirror having a mirror surface on an inside thereof;
a plurality of light-emitting units that radiate coherent light toward an edge of an object, the object being arranged in a vicinity of a first focal position of the elliptical mirror;
a photo detector that is arranged in a second focal position of the elliptical mirror and is capable of detecting the diffracted light resulting when the radiated coherent light is reflected by the edge of the object and by the elliptical mirror so as to arrive at the second focal position; and
a light-shielding member that shields low-order diffracted light which is regularly reflected among the diffracted light,
a plurality of the light-emitting units being provided in different positions in a thickness direction of the object, and each of a plurality of the light-emitting units being able to radiate the coherent light from a different direction, in a different radiation range in the thickness direction at the edge of the object.

3. The edge flaw detection device according to claim 1, wherein the light-emitting unit includes a light source that radiates the coherent light, and a condensing member that optically acts on the coherent light radiated from the light source so that the coherent light is radiated while the radiation range is reduced in the thickness direction at the edge of the object.

4. The edge detection device according to claim 1, wherein the light-emitting unit is able to radiate the coherent light at various wavelengths.

* * * * *